United States Patent
Ratner

(10) Patent No.: US 9,511,202 B1
(45) Date of Patent: Dec. 6, 2016

(54) BREATHING ASSISTANCE DEVICE WITH NEBULIZER

(71) Applicant: Mercury Enterprises, Inc., Clearwater, FL (US)

(72) Inventor: Jeffrey Bruce Ratner, Pinellas Park, FL (US)

(73) Assignee: Mercury Enterprises, Inc., Clearwater, FL (US)

( * ) Notice: Subject to any disclaimer, the term of this patent is extended or adjusted under 35 U.S.C. 154(b) by 931 days.

(21) Appl. No.: 13/693,638

(22) Filed: Dec. 4, 2012

(51) Int. Cl.
| | |
|---|---|
| *A61M 16/00* | (2006.01) |
| *A61M 15/00* | (2006.01) |
| *A61M 16/14* | (2006.01) |
| *A61M 11/02* | (2006.01) |
| *A61M 16/06* | (2006.01) |
| *A61M 16/08* | (2006.01) |
| *A61M 16/20* | (2006.01) |

(52) U.S. Cl.
CPC .............. *A61M 16/14* (2013.01); *A61M 11/02* (2013.01); *A61M 16/0057* (2013.01); *A61M 16/06* (2013.01); *A61M 16/0875* (2013.01); *A61M 16/20* (2013.01)

(58) Field of Classification Search
CPC .. A61M 11/02; A61M 16/0057; A61M 16/06; A61M 16/0875; A61M 16/201; A61M 11/06–11/08; A61M 15/00; A61M 15/002; A61M 15/0085–15/0087; A61M 16/14–16/168; B05B 7/0012; B05B 1/185; B05B 1/22; B05B 7/0408; B05B 7/0425; B67D 1/12; B67D 1/1252; E03C 1/084; F17C 1/005; F17C 7/00
See application file for complete search history.

(56) References Cited

U.S. PATENT DOCUMENTS

| | | | | | |
|---|---|---|---|---|---|
| 3,068,856 | A | * | 12/1962 | Bird ...................... | A61M 16/00 128/203.12 |
| 3,301,255 | A | * | 1/1967 | Thompson ............ | A61M 15/00 128/200.18 |
| 3,580,249 | A | * | 5/1971 | Takaoka ............... | A61M 16/125 128/200.14 |
| 3,584,621 | A | * | 6/1971 | Bird ...................... | A61M 16/00 128/200.18 |
| 3,658,059 | A | * | 4/1972 | Steil ....................... | A61M 11/06 128/200.21 |

(Continued)

*Primary Examiner* — Justine Yu
*Assistant Examiner* — Mark K Han
(74) *Attorney, Agent, or Firm* — Nicholas Pfeifer; Smith & Hopen, P.A.

(57) ABSTRACT

A breathing assistance device includes a patient breathing tube having a leading end in fluid communication with a face mask. A source of air under pressure is connected to a first port formed integrally with a valve in fluid communication with the breathing tube and a nebulizer is connected to a second port formed integrally with the valve. A compartment holding a medicinal compound in liquid fluid form is connected to the nebulizer. A valve actuator has an open position where gaseous fluid and aerosolized medicine from the nebulizer flow to the patient through the breathing tube and a closed position where only gaseous fluid without medication is delivered. Medication can therefore be administered to or withheld from the patient by manipulating the valve actuator. The valve construction enables the patient to exhale against pressure slightly above atmospheric pressure.

8 Claims, 7 Drawing Sheets

(56) References Cited

U.S. PATENT DOCUMENTS

| | | | | |
|---|---|---|---|---|
| 3,836,079 A * | 9/1974 | Huston | ................. | A61M 16/12 |
| | | | | 128/200.18 |
| 3,903,884 A * | 9/1975 | Huston | ................. | A61M 11/06 |
| | | | | 128/200.18 |
| 4,172,105 A * | 10/1979 | Miller | ................. | A61M 16/162 |
| | | | | 128/204.14 |
| 4,198,969 A * | 4/1980 | Virag | .................... | A61M 11/06 |
| | | | | 128/200.21 |
| 4,232,667 A * | 11/1980 | Chalon | ............ | A61M 16/1045 |
| | | | | 128/203.12 |
| 5,054,477 A * | 10/1991 | Terada | .................. | A61M 11/06 |
| | | | | 128/200.14 |
| 5,062,419 A * | 11/1991 | Rider | .................... | A61M 16/16 |
| | | | | 128/200.14 |
| 5,299,565 A * | 4/1994 | Brown | .................... | A62B 7/00 |
| | | | | 128/200.21 |
| 5,396,883 A * | 3/1995 | Knupp | ................. | A61M 16/20 |
| | | | | 128/200.14 |
| 5,570,682 A * | 11/1996 | Johnson | ................ | A61M 11/06 |
| | | | | 128/200.14 |
| 6,186,477 B1 * | 2/2001 | McCombs | ............ | A61M 16/20 |
| | | | | 128/205.24 |
| 7,191,780 B2 * | 3/2007 | Faram | ................ | A61M 16/127 |
| | | | | 128/200.14 |
| 7,634,995 B2 * | 12/2009 | Grychowski | .......... | A61M 11/06 |
| | | | | 128/200.14 |
| 7,841,335 B2 * | 11/2010 | Harrington | ............ | A61M 11/06 |
| | | | | 128/200.14 |
| 7,909,033 B2 * | 3/2011 | Faram | .................. | A61M 16/12 |
| | | | | 128/204.18 |
| 9,050,434 B2 * | 6/2015 | Faram | ............... | A61M 16/0875 |

* cited by examiner

BREATHING ASSISTANCE DEVICE WITH NEBULIZER

BACKGROUND OF THE INVENTION

1. Field of the Invention

This invention relates, generally, to devices that help patients breathe. More particularly, it relates to a breathing assistance device that includes a nebulizer but which does not require a second flow valve connection.

2. Description of the Prior Art

A conventional breathing assistance device delivers preselected gaseous fluids suitable for breathing to a patient who requires breathing assistance. The preselected gaseous fluids are stored under pressure in a tank which may hold oxygen or miscellaneous mixtures of suitable gaseous fluids. The patient wears a facemask and a tube interconnects the tank and the facemask. A manometer and a pressure relief valve are typically provided between the tank and the facemask and such parts perform their respective well-known functions.

There are times when a physician may want to employ a nebulizer to administer therapeutic dosages of medicine to a patient suffering from breathing difficulties.

There are two (2) problems associated with the prior art use of nebulizers. First, the flow of gaseous fluid to the patient must be interrupted so that a nebulizer can be added to the system. Secondly, the nebulizer must be connected to a second tank of gaseous fluid if the tank already in use does not have a "Y" connection so that the nebulizer flow valve can be attached thereto.

Thus there is a need for a breathing assistance device that enables a patient to receive medicinal treatment from a nebulizer without interrupting the flow of gaseous fluid to the patient.

There is also a need for a system that does not require connection to a second flow valve associated with a second tank.

Moreover, there is a need for a system that does not require that a tank in use be equipped with a "Y" connection so that a second flow valve can be connected to it.

In view of the art considered as a whole at the time the present invention was made, it was not obvious to those of ordinary skill how a medicinal treatment could be administered to a patient wearing a breathing assistance device without requiring a second tank or a tank with a "Y" connection.

SUMMARY OF THE INVENTION

The long-standing but heretofore unfulfilled need for a breathing assistance device that is used with a single tank having a single flow control valve and which does not require interruption of flow of gaseous fluid to a patient is now met by a new, useful, and non-obvious invention.

The novel breathing assistance device includes a patient breathing tube having a leading end adapted to be in open fluid communication with a face mask worn by a patient requiring breathing assistance.

A nebulizer port is connected to or formed integrally with the patient breathing tube. In a preferred embodiment, the nebulizer port extends radially from the patient breathing tube.

A nebulizer has a leading end formed integrally with or releasably attachable to the nebulizer port. The nebulizer includes a compartment that holds a medicinal compound in liquid fluid form.

A valve body is mounted to the patient breathing tube, preferably to the trailing end of the patient breathing tube and preferably in axial alignment therewith.

A first port is in open fluid communication with the valve body. In a preferred embodiment, the first port extends radially relative to longitudinal axis of the valve body but any other orientation is within the scope of this invention.

A first tube has a trailing end connected in open fluid communication to a remote source of gaseous fluid under pressure and has a leading end connected in open fluid communication to the first port.

A second port is also in open fluid communication with the valve body. In a preferred embodiment, the second port extends radially relative to the longitudinal axis of the valve body in circumferentially spaced relation to the first port but any other orientation of said second port relative to the valve body and the first port is within the scope of this invention.

A second tube has a trailing end connected in open fluid communication to the second port and has a leading end connected in open fluid communication to a trailing end of the nebulizer, i.e., to the liquid fluid-holding compartment of the nebulizer.

A valve positioned between the tank and the face mask has a closed position that prevents flow of gaseous fluid through the second tube and an open position that enables flow of gaseous fluid through the second tube. The position of the valve has no effect on the flow of gaseous fluid from the tank to the facemask through the first tube.

The valve may be a gate valve, a butterfly valve, or any other type of valve that is suitable for a flow of liquid fluid. It may be selectively opened and closed by any suitable valve actuator such as a hand-operated rotatable valve actuator, a hand-operated slide valve actuator, a hand operated toggle valve actuator, and the like. The selected type of valve actuator may also be operated by electrical or electronic means but a hand-operated valve actuator is preferred.

In a preferred embodiment, the valve has a handle that is rotatably mounted relative to a longitudinal axis of the patient breathing tube and the valve body. In this preferred embodiment, a ninety degree (90°) rotation of the handle in a first direction opens the valve and allows gaseous fluid to flow through the second tube and the same amount of rotation in the opposite direction closes the second tube to such flow.

Accordingly, the novel breathing assistance device delivers gaseous fluid under pressure from the remote tank to a patient when the valve is in its closed position, just as if no nebulizer was incorporated into the system.

The novel breathing assistance device delivers gaseous fluid under pressure from the remote tank to the patient, together with aerosol from the nebulizer, when the valve is in its open position. The spray of medicinal fluid from the nebulizer is entrained into the flow of air flowing through the patient breathing tube en route to the patient's face mask.

In a preferred embodiment, the valve includes a shaft formed integrally therewith. The shaft is axially displaced when the valve is rotated. A pair of O-rings is mounted on the shaft in longitudinally spaced relation to one another to provide a sealing function when the valve is closed, said sealing function preventing flow of gaseous fluid through the second tube. The O-rings provide no sealing function when the valve is open so that gaseous fluid flows under pressure through the second tube to the nebulizer In the preferred embodiment, a plurality of ramps is formed integrally with the trailing end of the valve. The handle has a disc-shaped leading end and a plurality of pins is formed integrally with said disc-shaped leading end and said pins extend radially outwardly with respect to a longitudinal axis of the device.

The valve cover has a mating plurality of ramps formed therein that match in size, quantity and slope the size, quantity and slope of ramps formed in the trailing end of the valve.

The pins are sandwiched between the ramps formed in the trailing end of the valve and the ramps formed in the leading end of the valve cover. The pins slide up their associated ramps when the valve handle is rotated from a first position to a second position and the pins slide down their associated ramps when the valve handle is rotated from said second position to the first position. This constrains the shaft to displace axially along its longitudinal axis as the valve handle is rotated.

Any electrical, electronic, hydraulic or mechanical means for translating rotational movement of a valve handle to axial translation of a shaft for the purpose of opening and closing a valve is within the scope of this invention.

Moreover, any electrical, electronic, hydraulic or mechanical means for opening and closing a valve that controls the path of travel of gaseous fluid is within the scope of this invention. The heart of the invention resides in the ability for a care-giver to switch between a main gaseous flow from a single remote tank having a single flow valve with no "Y" connection to a patient where a nebulizer is bypassed to gaseous flow from the same single remote tank to the patent where at least some of the gaseous flow is routed through a nebulizer without interrupting the main gaseous flow.

An orifice jet is disposed concentrically within a lumen of the patient breathing tube and said orifice jet is in open fluid communication with the remote source of gaseous fluid under pressure when the valve is open and when the valve is closed.

A plurality of slots or preferably rectangular openings is formed in a leading end of the valve body, said openings enabling the patient to exhale into ambient atmosphere when the nebulizer valve is open or closed.

The patient receives a combination of gaseous fluid from the orifice jet and entrained ambient air through the openings when the patient inhales at a rate greater than the rate that gaseous fluid is delivered from the remote source of gaseous fluid under pressure and no gaseous fluid is flowing through the nebulizer tube.

The patient receives a combination of gaseous fluid from the orifice jet, entrained room air through the openings formed in the leading end of said valve, and from the nebulizer, together with aerosolized medication if gaseous fluid is flowing through said nebulizer.

An important object of the invention is to enable a patient wearing a facemask and receiving assistance in breathing to receive medication as needed without interruption of the flow of gaseous fluids to the patient.

Another object is to provide a breathing assistance device that is equipped with a built-in nebulizer having a manually operated "on/off" or "open/closed" valve.

An object related to the foregoing object is to provide a breathing assistance device equipped with a built-in nebulizer that operates from a single remote tank having a single flow valve.

Another object is to provide a breathing assistance device that delivers aerosolized medication to a patient when the nebulizer valve is "open" and which does not deliver said aerosolized medication when the nebulizer valve is "closed."

Still another object is to provide a breathing assistance device that enables a patient to exhale against a pressure greater than atmospheric pressure.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the nature and objects of the invention, reference should be made to the following detailed disclosure, taken in connection with the accompanying drawings, in which.

DETAILED DESCRIPTION OF THE PREFERRED EMBODIMENT

Figure 1:
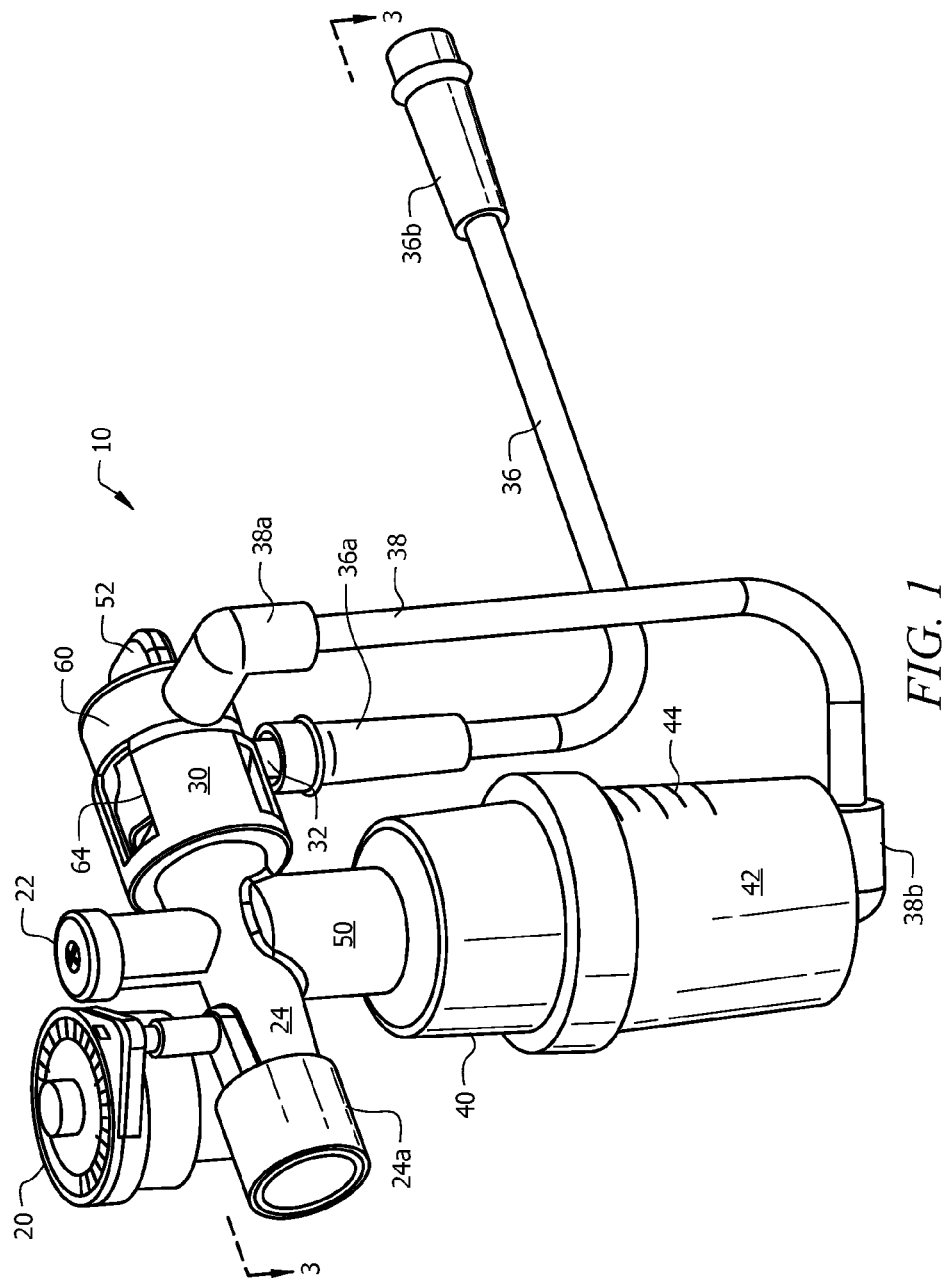
FIG. 1 is a front perspective view of the novel structure.

FIG. 1 depicts an illustrative embodiment of the novel structure which is denoted as a whole by the reference numeral 10.

The novel structure includes manometer 20 and pressure relief valve 22, both of said components performing the well-known functions expressed by their respective names.

Patient breathing tube 24 is in open fluid communication at its leading end 24a with a face mask worn by a patient. Manometer 20 and pressure relief valve 22 are in open fluid communication with said patient breathing tube.

Novel valve body 30 is mounted to the trailing end of patient breathing tube 24 and ports 32, 34 are preferably formed integrally with said novel valve body. Port 34 is concealed in FIG. 1 by elbow 38a.

In this preferred embodiment, port 32 is vertically disposed and depends from valve body 30 as depicted. Port 34 is preferably horizontally disposed as indicated. Neither the vertical disposition of port 32 nor the horizontal disposition of port 34 is critical. Ports 32 and 34 are radially disposed relative to a longitudinal axis of valve body 30 to facilitate attachment of conduits thereto but such radial disposition is not critical.

Port 32 provides a mount for elongate, flexible conduit 36 that is connected at its enlarged trailing end 36b to a remote source of gaseous fluid under pressure, not depicted, and to port 32 at its enlarged leading end 36a.

Port 34 provides a mount for elongate, flexible conduit 38 that is connected to nebulizer compartment 42 at its enlarged trailing end 38b and to port 34 at its enlarged leading end 38a.

Nebulizer 40 has a conventional structure and therefore includes transparent or translucent compartment 42 having graduation marks 44 imprinted thereon. A medicinal compound in liquid fluid form selected by a physician is charged into nebulizer compartment 42 prior to connection of leading end 24a of breathing tube 24 to a connecting port, not depicted, formed in a patient's face mask, not shown.

Nebulizer 40 transforms the liquid fluid in nebulizer container 42 into a mist or spray in a way that is well-known outside the context of breathing assistance devices, i.e., nebulizers are known for use in connection with spray bottles that dispense a wide variety of liquid fluids in spray or mist form.

Port 50 is preferably formed integrally with patient breathing tube 24 and preferably depends vertically therefrom in parallel relation to port 32 as depicted. The leading end of nebulizer 40 is mounted to said port 50 so that the medicinal compound in compartment 42 is in spray or mist form when it enters patient breathing tube 24.

Valve actuator 52 is rotatably mounted relative to the longitudinal axis of symmetry of patient breathing tube 24 and valve 30. It has a closed position that prevents flow of gaseous fluid through tube 38 and an open position that enables flow of gaseous fluid through tube 38.

When valve actuator 52 is in the closed position, novel breathing assistance device 10 operates in a conventional manner, i.e., it delivers gaseous fluid under pressure to a patient. Gaseous fluid under pressure flows from the remote source of gaseous fluid under pressure to the patient's face mask through conduit 36 and patient breathing tube 24.

Figure 6A:
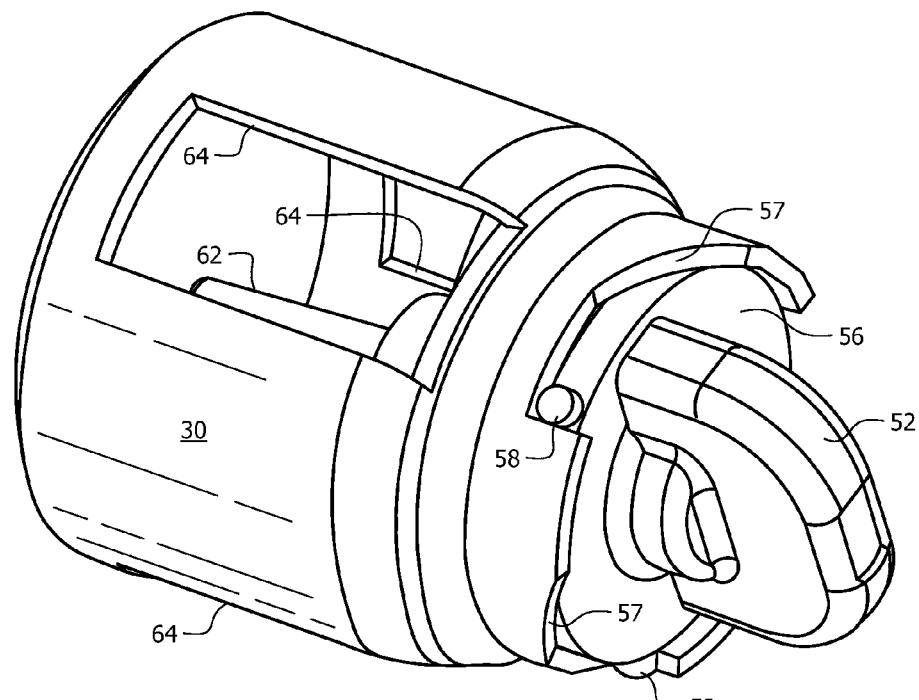
FIG. 6A is a perspective view of the novel components when the flow control valve is in its closed configuration.

The closed position of valve actuator 52 prevents flow of gaseous fluid through conduit 38 and no liquid medication in nebulizer compartment 42 can enter into the atomizing part of nebulizer 40. The closed position of valve actuator 52 is depicted in FIGS. 2B and 6A.

Figure 2:
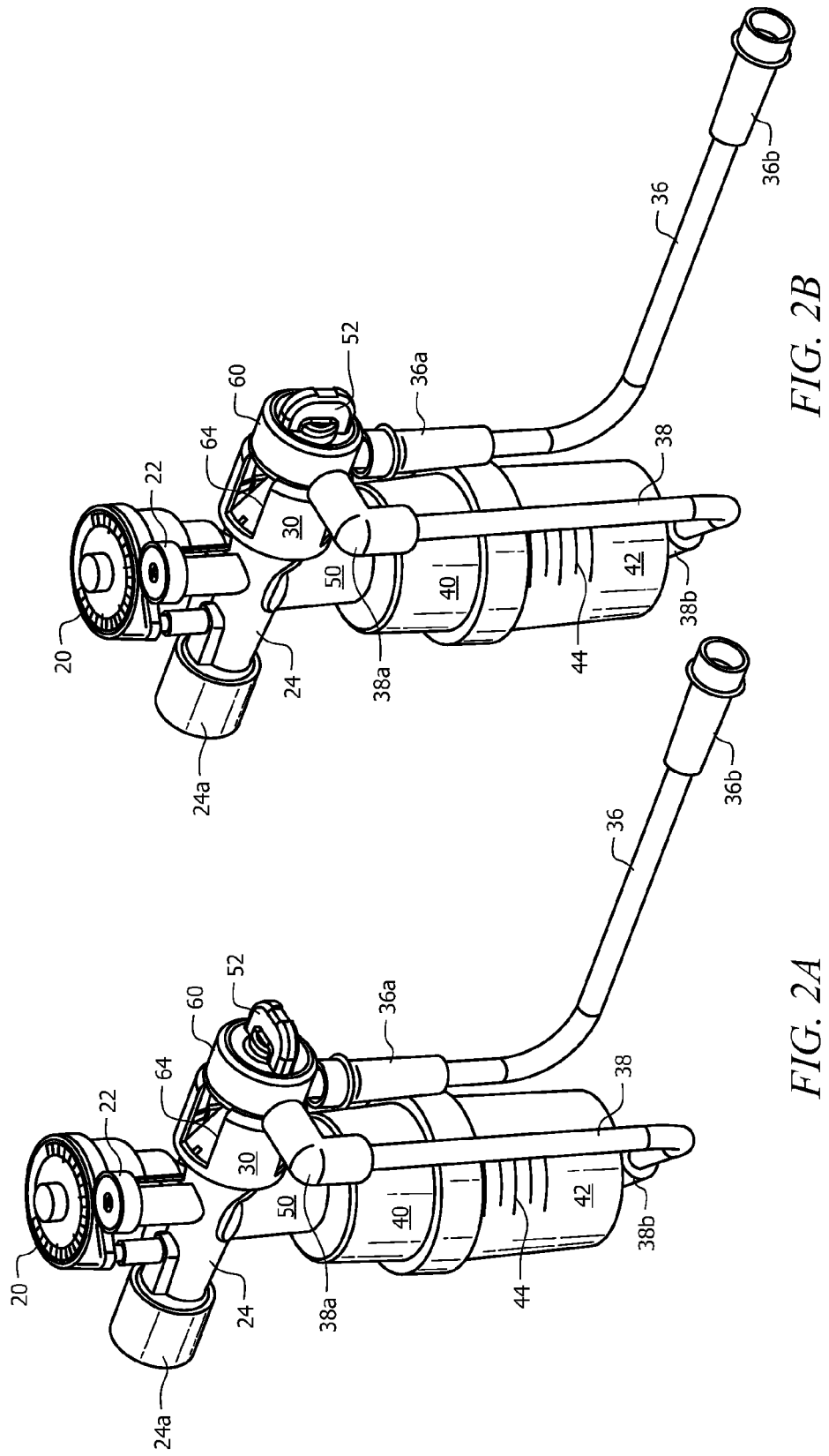
FIG. 2A is a first rear perspective view thereof, depicting a flow control valve in its open position.
FIG. 2B is a second rear perspective view thereof, depicting the flow control valve in its closed position.
Figure 3:
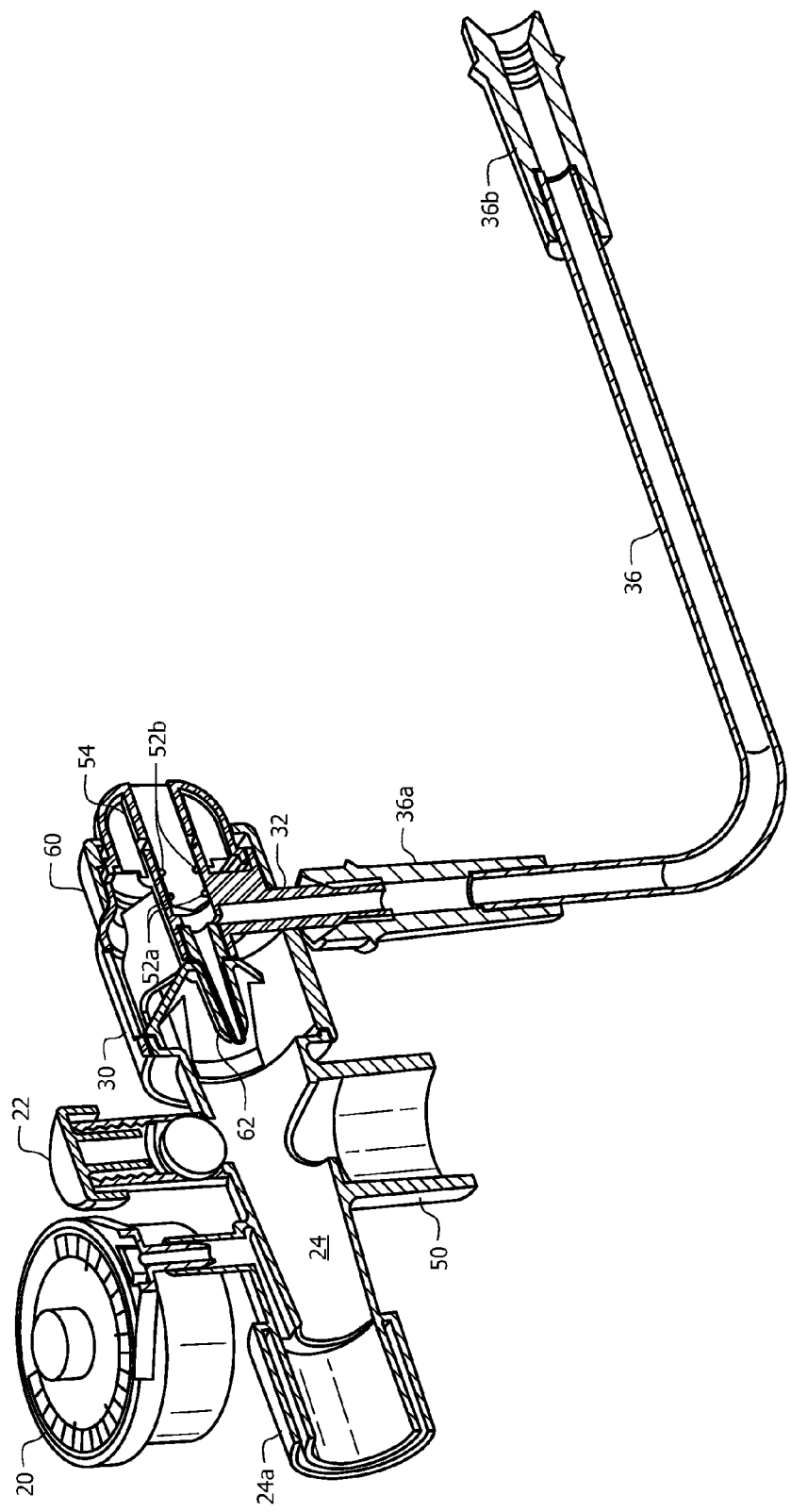
FIG. 3 is a longitudinal sectional view taken along line 3-3 in FIG. 1.
Figure 6B:
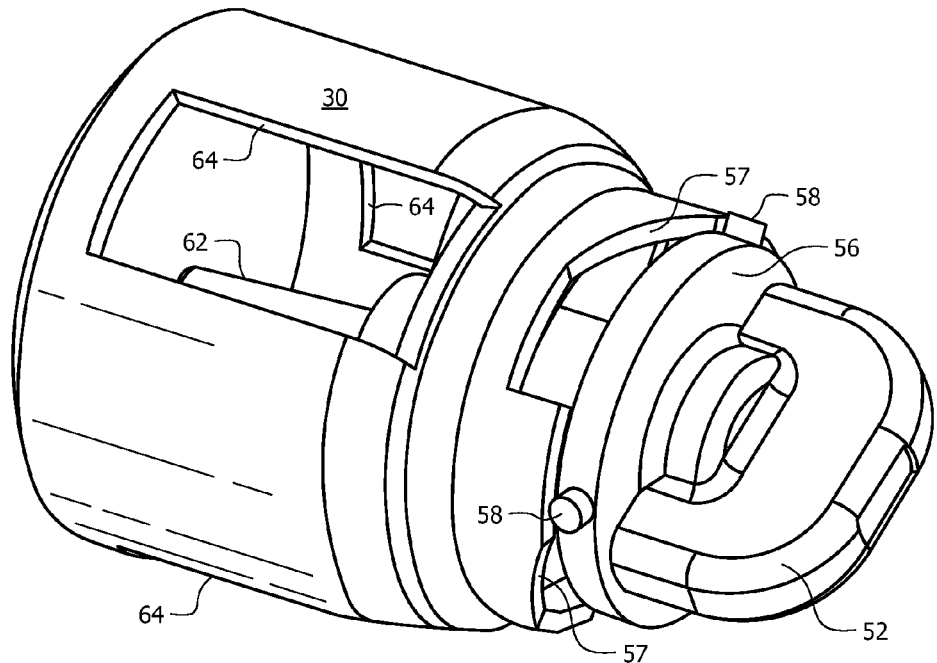
FIG. 6B is a perspective view of the novel components when the flow control valve is in its open configuration.

When valve actuator 52 is in the open position as depicted in FIGS. 1, 2A and 6B, gaseous fluid under pressure continues to flow from the remote source of gaseous fluid under pressure to the patient's face mask through patient breathing tube 24. Said gaseous fluid under pressure also flows through tube 38 to nebulizer 40. This causes liquid fluid in nebulizer compartment 42 to flow through nebulizer 40 so that the liquid fluid is changed into a mist or spray that is introduced into the lumen of patient breathing tube 24. That mist or spray of the medicinal compound is entrained into the flow of gaseous fluid flowing through patient breathing tube 24 en route to the patient's face mask.

Figure 5A:
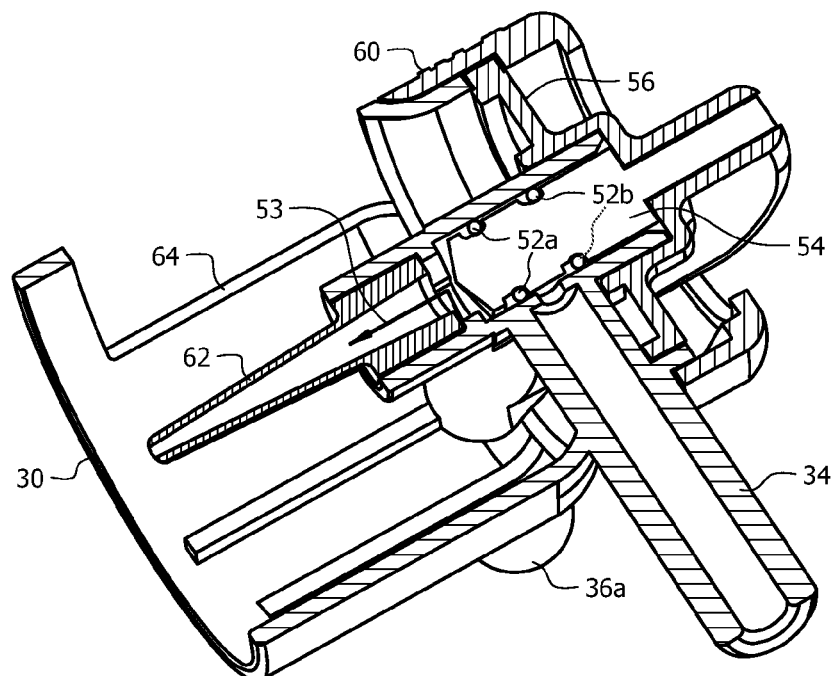
FIG. 5A is a sectional view taken along line 5A-5A in FIG. 4A.
Figure 5B:
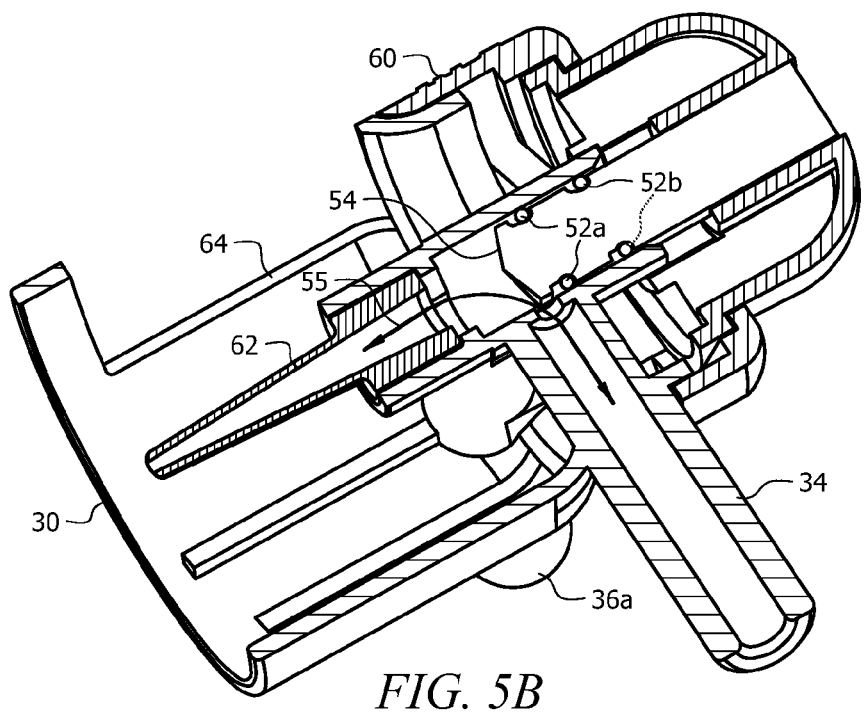
FIG. 5B is a sectional view taken along line 5B-5B in FIG. 4B.

O-rings 52a, 52b, depicted in FIGS. 5A and 5B, are mounted on shaft 54 and provide a sealing function when valve actuator 52 is in its closed position. More particularly, shaft 54 is axially displaced when valve actuator 52 is rotated, as understood by comparing the axial position of shaft 54 in FIG. 5A (shaft extended, flow cut off) with its position in FIG. 5B (shaft retracted). Single-headed directional arrow 53 in FIG. 5A indicates the flow of gaseous fluid when shaft 54 is extended, and double headed directional arrow 55 in FIG. 5B indicates the flow of gaseous fluid when shaft 54 is retracted, i.e., when valve actuator 52 is in its open position and gaseous fluid is flowing through second tube 38 as well as through first tube 36.

Figure 4A:
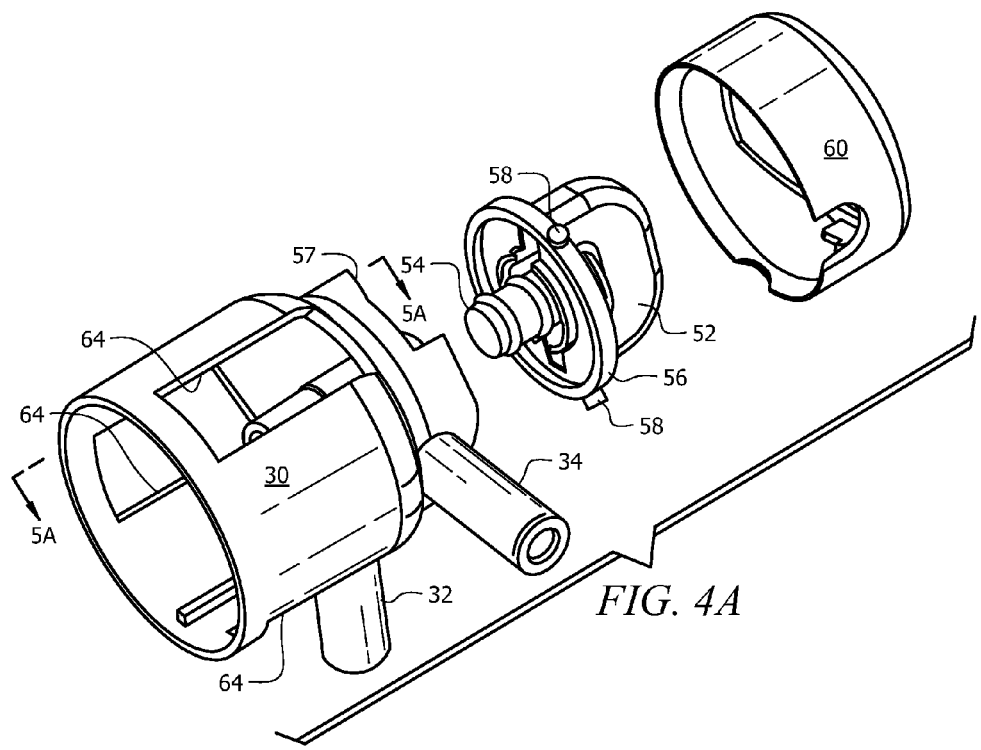
FIG. 4A is an exploded front perspective view of the novel components.
Figure 4B:
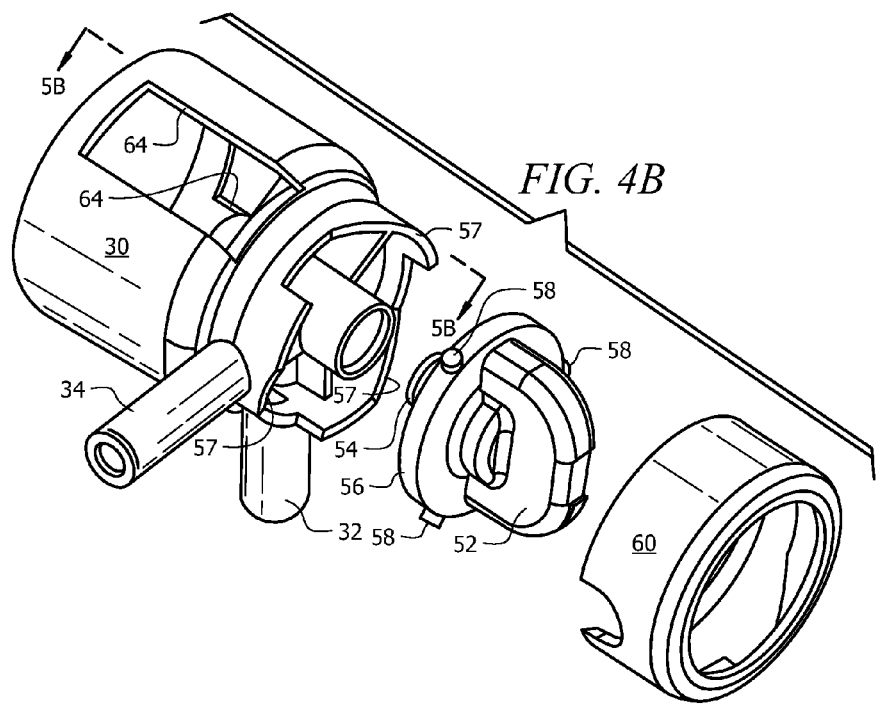
FIG. 4B is an exploded rear perspective view of the novel components.
Figure 7:
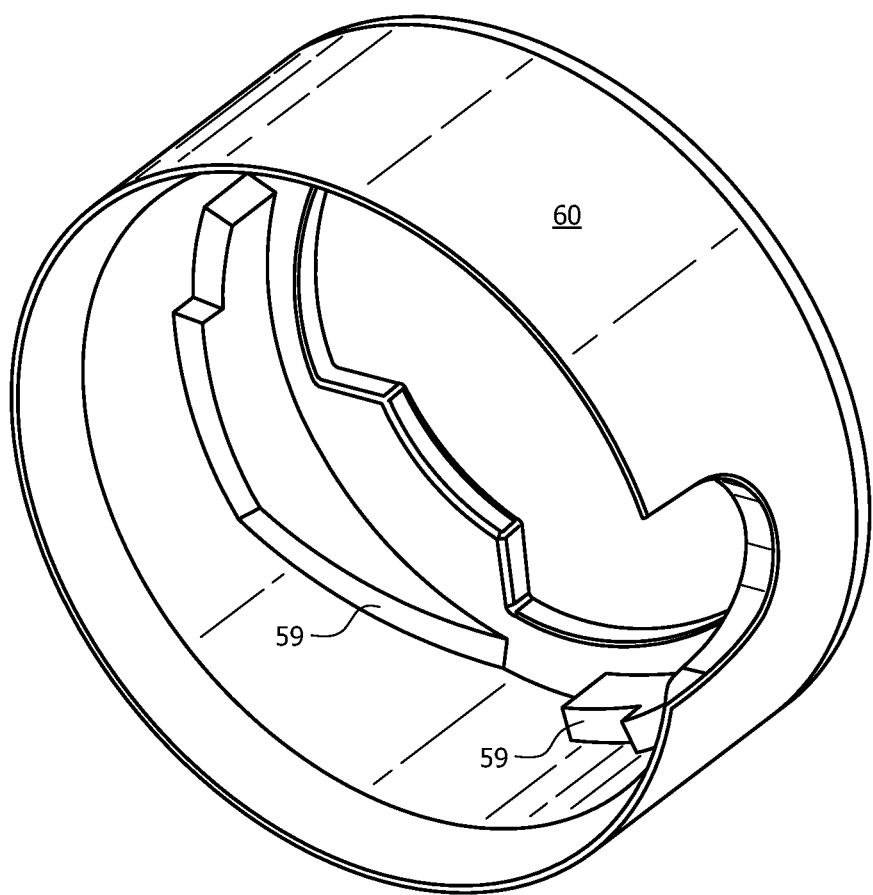
FIG. 7 is a perspective view of the novel valve cover.

Although there are multiple well-known ways to translate rotational movement of a rotatably mounted valve actuator to axial movement of a shaft to which said valve actuator is connected, the preferred structure as best depicted in FIGS. 4B and 7 includes a plurality of circumferentially spaced apart ramps, collectively denoted 57, that are formed integrally with the trailing end of valve body 30 and a plurality of circumferentially spaced apart pins 58 that are formed integrally with disc 56 which is formed integrally with valve actuator 52.

More particularly, the preferred embodiment includes three (3) ramps, collectively denoted 57 in FIG. 4B, and three (3) pins, collectively denoted 58 in FIGS. 4A and 4B. Each pin is formed integrally with disc 56 and extends radially outwardly with respect to a longitudinal axis of shaft 54.

Each pin 58 thus slides up or down its associated ramp 57, depending upon the direction of rotation of valve actuator 52 as it travels from its open to closed position or vice versa.

Valve knob cover 60, depicted in FIGS. 4A, 4B and 7, also has three (3) ramps, collectively denoted 59, formed therein that cooperate with ramps 57 so that each pin 58 is sandwiched between two (2) ramps to constrain shaft 54 to displace axially along said longitudinal axis of symmetry as valve actuator 52 is rotated.

If valve actuator 52 is in its "nebulizer open" position, as depicted in FIGS. 1, 2A and 6B, the patient receives a combination of gaseous fluid from three (3) sources: 1) orifice jet 62; 2) entrained room air through three (3) circumferentially spaced apart rectangular openings, collectively denoted 64, formed in valve body 30; and 3) nebulizer 40, together with aerosolized medication.

If valve actuator 52 is in it "nebulizer off" position, as depicted in FIGS. 2B and 6A, the patient receives a combination of gaseous fluid from two (2) sources: 1) orifice jet 62; and 2) entrained room air through said three (3) rectangular openings 64.

When the patient exhales, gaseous fluid flows out rectangular openings 64. Thus the patient exhales against a pressure slightly above atmospheric pressure due to the continuing incoming flow of gaseous fluids.

The novel structure thus requires no interruption of gaseous fluid flow to a patient when switching from a medicated flow of gaseous fluid to a non-medicated flow, or vice versa. Nor does the novel structure require a second remote tank having a flow valve to enable connection to a nebulizer. Moreover, it does not require a single remote tank having a "Y" connection for connection of a second flow valve to enable connection to a nebulizer.

It will thus be seen that the objects set forth above, and those made apparent from the foregoing disclosure, are efficiently attained and since certain changes may be made in the above construction without departing from the scope of the invention, it is intended that all matters contained in the foregoing disclosure or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:
1. A breathing assistance device, comprising:
   a patient breathing tube having a leading end adapted to be in open fluid communication with a face mask worn by a patient requiring breathing assistance;
   a valve body in open fluid communication with said patient breathing tube;
   a nebulizer port in open fluid communication with said patient breathing tube;
   a nebulizer having a leading end in open fluid communication with said nebulizer port;
   said nebulizer including a nebulizer compartment adapted to hold a medicinal compound in liquid fluid form;

a first port in open fluid communication with said valve body;

a first tube having a trailing end connected in open fluid communication to a remote source of gaseous fluid under pressure and having a leading end connected in open fluid communication to said first port;

a second port in valved communication with said valve body;

a second tube having a trailing end connected in open fluid communication with said second port and having a leading end connected in open fluid communication with said nebulizer compartment;

a valve actuator having a closed position that allows gaseous fluid flow through said first tube and prevents flow of gaseous fluid through said second tube;

said valve actuator having an open position that enables flow of gaseous fluid flow through said first tube and through said second tube;

said breathing assistance device adapted to deliver gaseous fluid under pressure to the patient when said valve actuator is in said closed position, said gaseous fluid under pressure flowing from said remote source of gaseous fluid under pressure through said first tube to said patient breathing tube; and said breathing assistance device adapted to deliver gaseous fluid under pressure to the patient when said valve actuator is in said open position, said gaseous fluid under pressure flowing from said remote source of gaseous fluid under pressure through said first tube to said patient breathing tube, and flowing to said nebulizer through said second tube, causing said medicinal compound in said nebulizer compartment to flow through said nebulizer so that said medicinal compound is changed into a spray that is introduced into said patient breathing tube, said spray of medicinal compound being entrained into the flow of gaseous fluid flowing through said patient breathing tube en route to said patient's face mask.

2. The breathing assistance device of claim 1, further comprising:

said valve actuator including a shaft formed integrally therewith;

a pair of O-rings mounted on said shaft in longitudinally spaced relation to one another to provide a sealing function when said valve actuator is in said closed position, said sealing function preventing flow of gaseous fluid through said second tube when said valve actuator is in said closed position and said O-rings providing no sealing function so that gaseous fluid may flow under pressure through said second tube to said nebulizer compartment when said valve actuator is in said open position.

3. The breathing assistance device of claim 2, further comprising:

said shaft being axially displaced when said valve actuator is rotated.

4. The breathing assistance device of claim 3, further comprising:

a plurality of ramps formed integrally with the trailing end of said valve body;

said valve actuator having a disc formed integrally therewith, said disc being disposed transverse to a longitudinal axis of said valve body;

a plurality of pins formed integrally with said disc and projecting radially therefrom;

a valve body cover having a plurality of ramps formed therein that match in quantity the quantity of ramps formed in said trailing end of said valve body;

said pins being sandwiched between the ramps formed in said valve body and the ramps formed in said valve body cover to constrain said shaft to displace axially along said longitudinal axis as said valve actuator is rotated;

said pins sliding up their associated ramps when said valve actuator is rotated from a first position to a second position and said pins sliding down their associated ramps when said valve actuator is rotated from said second position to said first position.

5. The breathing assistance device of claim 1, further comprising:

an orifice jet disposed concentrically within a lumen of said patient breathing tube;

said orifice jet being in open fluid communication with said remote source of gaseous fluid under pressure when said valve actuator is in its open position and when said valve actuator is in its closed position.

6. The breathing assistance device of claim 1, further comprising:

a plurality of openings formed in said valve body;

said plurality of openings enabling the patient to exhale into ambient atmosphere;

said patient receiving a combination of gaseous fluid from an orifice jet and entrained ambient air through said plurality of openings if said patient inhales at a rate greater than the rate that gaseous fluid is delivered from said remote source of gaseous fluid under pressure and no gaseous fluid is flowing through said second tube.

7. The breathing assistance device of claim 6, further comprising:

said patient receiving a combination of gaseous fluid from said orifice jet, entrained room air through said plurality of openings, and from the nebulizer, together with aerosolized medication if gaseous fluid is flowing through said second tube and if said patient inhales at a rate greater than the rate that gaseous fluid is delivered from said remote source of gaseous fluid under pressure.

8. The breathing assistance device of claim 1, further comprising:

said first and second ports extending radially from said valve body in circumferentially spaced relation to one another.

* * * * *